(12) United States Patent
Ahn et al.

(10) Patent No.: US 9,669,114 B2
(45) Date of Patent: Jun. 6, 2017

(54) CONTRAST MEDIUM COMPOSITION AND METHOD OF BIO IMAGINATION USING THE SAME

(71) Applicant: KOREA INSTITUTE OF SCIENCE AND TECHNOLOGY, Seoul (KR)

(72) Inventors: Dae Ro Ahn, Paju-si (KR); Se Hoon Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 100 days.

(21) Appl. No.: 14/197,322

(22) Filed: Mar. 5, 2014

(65) Prior Publication Data

US 2014/0255307 A1 Sep. 11, 2014

(30) Foreign Application Priority Data

Mar. 7, 2013 (KR) ........................ 10-2013-0024657

(51) Int. Cl.
*A61B 10/00* (2006.01)
*A61B 5/00* (2006.01)
*A61B 8/00* (2006.01)
*A61K 49/00* (2006.01)

(52) U.S. Cl.
CPC ...... *A61K 49/0093* (2013.01); *A61K 49/0002* (2013.01); *A61K 49/0032* (2013.01); *A61K 49/0054* (2013.01)

(58) Field of Classification Search
CPC ................ A61K 49/00; A61K 49/0056; A61K 41/0057; A61K 49/0021; A61K 49/0013; A61K 49/0017; A61K 49/0019; A61K 49/0023; A61K 49/0034; A61K 49/0026; A61K 49/0028; A61K 49/003; A61K 49/0036; A61K 49/0039; A61K 49/0041; A61K 49/0043; A61K 49/0002; A61K 49/0032; A61K 49/0054; A61K 49/0093

USPC ........ 424/1.11, 1.65, 1.81, 9.1, 9.3, 9.4, 9.5, 424/9.6, 1.73
See application file for complete search history.

(56) References Cited

FOREIGN PATENT DOCUMENTS

KR 10-2010-0030194 A 3/2010
WO WO 2012/153273 A 11/2012

OTHER PUBLICATIONS

Grobmyer et al, 2010, Cancer Nanotechnology, Chapter 6 (written by Au et al): Gold Nanocages for Cancer Imaging and Therapy,pp. v-viii and 83-99.*
Kim et al, 2013, Biomaterials, vol. 34, pp. 5226-5235.*
Li et al, 2011, Interface Focus, vol. 1, pp. 702-724.*
Korean Notice of Allowance issued Jan. 12, 2015 in counterpart Application No. KR 10-2013-0024657 (2 pages, in Korean).
Korean Office Action issued Jun. 12, 2014 in counterpart Korean Application No. KR 10-2013-0024657 (6 pages, in Korean).

* cited by examiner

*Primary Examiner* — D L Jones
(74) *Attorney, Agent, or Firm* — NSIP Law

(57) ABSTRACT

The present invention relates to contrast medium composition and a method of bio imagination using the same. The contrast medium composition of the present invention includes a biomolecule, DNA nanostructure, as an active ingredient, is fundamentally non-cytotoxic and non-immunogenic and is not likely to induce safety problems that may be observed in other organic or inorganic contrast medium composition. In addition, the contrast medium composition of the present invention not only facilitates diagnosis of disease through sufficient contrast enhancement effect by showing excellent cellular uptake and intracellular stability and can visualize even SLNs which is difficult to be visualized traditionally, so can judge metastasis of cancer easily and apply lower invasive treatment.

11 Claims, 14 Drawing Sheets

CONTRAST MEDIUM COMPOSITION AND METHOD OF BIO IMAGINATION USING THE SAME

SEQUENCE LISTING

The instant application contains a Sequence Listing which has been submitted electronically in ASCII format and is hereby incorporated by reference in entirety. Said ASCII copy, created on May 13, 2014, is named 021059.0028_SL.txt and is 2905 bytes in size.

CROSS REFERENCE TO RELATED APPLICATIONS

This application claims priority from Korean Patent Application No. 10-2013-0024657 filed on Mar. 7, 2013 in the Korean Intellectual Property Office, the disclosure of which is incorporated herein by reference in its entirety.

BACKGROUND OF THE INVENTION

1. Field of the Invention

The present invention relates to contrast medium composition and a method of bio imagination using the same.

2. Background of the Invention

Sentinel lymph nodes (SLNs) are the first lymph nodes which cancer cells reach after traveling through lymphatic vessels from the primary tumor. Evaluating the nodal status is crucial in accurate staging of human cancers and accordingly determines prognosis and the most appropriate treatment. While patients with breast cancer and melanoma are currently subject to invasive sentinel lymph node biopsy (SLNB) to stage metastases, alternative noninvasive methods have been pursued. In particular, noninvasive imaging methods based on the blue dyes and radioactive colloids are the major methods for identification of SLNs in clinical research since they were introduced about two decades ago. Although these methods are being used widely, there are drawbacks in each method. Owing to the spectral limit of the blue dyes, SLNs cannot be identified without a skin incision. Since the dyes are small sized molecules, they are quickly drained from the initial loading point. This rapid diffusion property, however, becomes disadvantageous for staying in the SLN area surrounded by permeable lymphatic vessels. After short retention in SLN (ca. 15-20 min), the dyes pass to secondary nodes, causing difficulties in distinguishing selectively SLNs from other subsequent nodes. Recently, indocyanine green (ICG), a near infrared (NIR) dye, has been employed to circumvent the optical drawback of the blue dyes. While improvement in macroscopic detection of SLNs was achieved by using ICG, the short retention issue could not be addressed since ICG is also a small dye. In contrast to the small dye-based imaging agents, the radioisotope-labeled colloids including the $^{99m}$Tc-labeled sulfur colloid have a relatively slow diffusion rate and thus tend to remain at the site of administration. Because of this slow diffusion, it takes a long time for the colloids to arrive at a lymph node and should therefore be injected the day before the operation for lymphatic mapping. Additionally, this radioisotope method can be used in limited places because of the safety regulations for radioactive agents. To overcome these drawbacks observed in the conventional dye-guided or radio-guided SLN mapping methods, noninvasive imaging modalities such as ultrasound, computed tomography (CT), magnetic resonance imaging, optical imaging, photoacoustic tomography have been investigated for identification of SLNs. These newly studied methods utilize mainly nanoparticle-based imaging agents, since they show relatively quick arrival at the lymph node site compared to the colloids of radionuclide and extended retention time at the SLN area compared to the small dyes. Inorganic or polymer nanoparticles, however, have a potential to be toxic in vivo since they are made from biologically unnatural materials.

Previously, it has been shown that inherently biocompatible DNA could self-assemble to construct various three dimensional (3D) DNA nanocages including tetrahedra, bipyrimids, octahedra, dodecahedra and fullerene-like structures. Among them, the DNA tetrahedron has been considered one of the most practical DNA nanocages since it can be assembled simply from four DNA strands and prepared in high yield. The recent demonstration about cellular uptake of the DNA tetrahedron into mammalian cells has opened a great opportunity for the nanocage to play important roles in biomedical applications. In addition, the tetrahedron is significantly nuclease resistant, which makes the DNA tetrahedron even a more attractive tool for in vivo imaging technology. Although previous studies demonstrated that the DNA nanocages could become a promising tool for studying biotechnology such as drug delivery and stimulation of immune response at an in vitro cellular level, in vivo applications of the 3D DNA nanoconstructs is still in its infancy. Regarding this, siRNA-loaded DNA tetrahedra were very recently developed and used for effective mRNA regulation in an in vivo system as a pioneering study.

This application seeks priority to and incorporates by reference the following U.S. pending provisional patent applications. Methods and materials similar or equivalent to those described herein can be used in the practice or testing of embodiments of the present invention. All publications mentioned herein are incorporated by reference in their entirety. The documents, patents and patent applications referred to herein are hereby incorporated by reference.

SUMMARY OF THE INVENTION

Inventors of the present invention have studied and given effort to develop a contrast medium composition that not only is introduced into inside of cells and has prolonged retention time but also is harmless to human body. As the results, they completed the present invention by identifying that inherently biocompatible 3-dimensional DNA nanostructure had improved cellular uptake and stability, so could be used for in vivo bio imagination very usefully.

Accordingly, an object of the present invention is to provide a contrast medium composition applying the 3 dimensional DNA nanostructure.

Another object of the present invention is to provide a bio imagination method using the contrast medium composition.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

Cy5-S4, S3, S2, and S1. DLS data to estimate hydrodynamic sizes of Td (B) and Ds (C). AFM images of Td and height distribution of the Td particles in AFM images.

Figure 2:
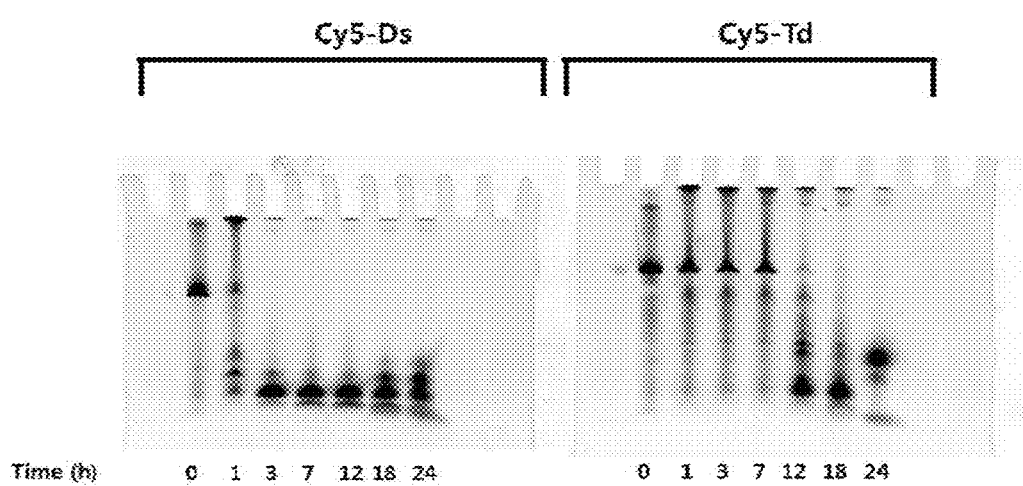
Figure 3:
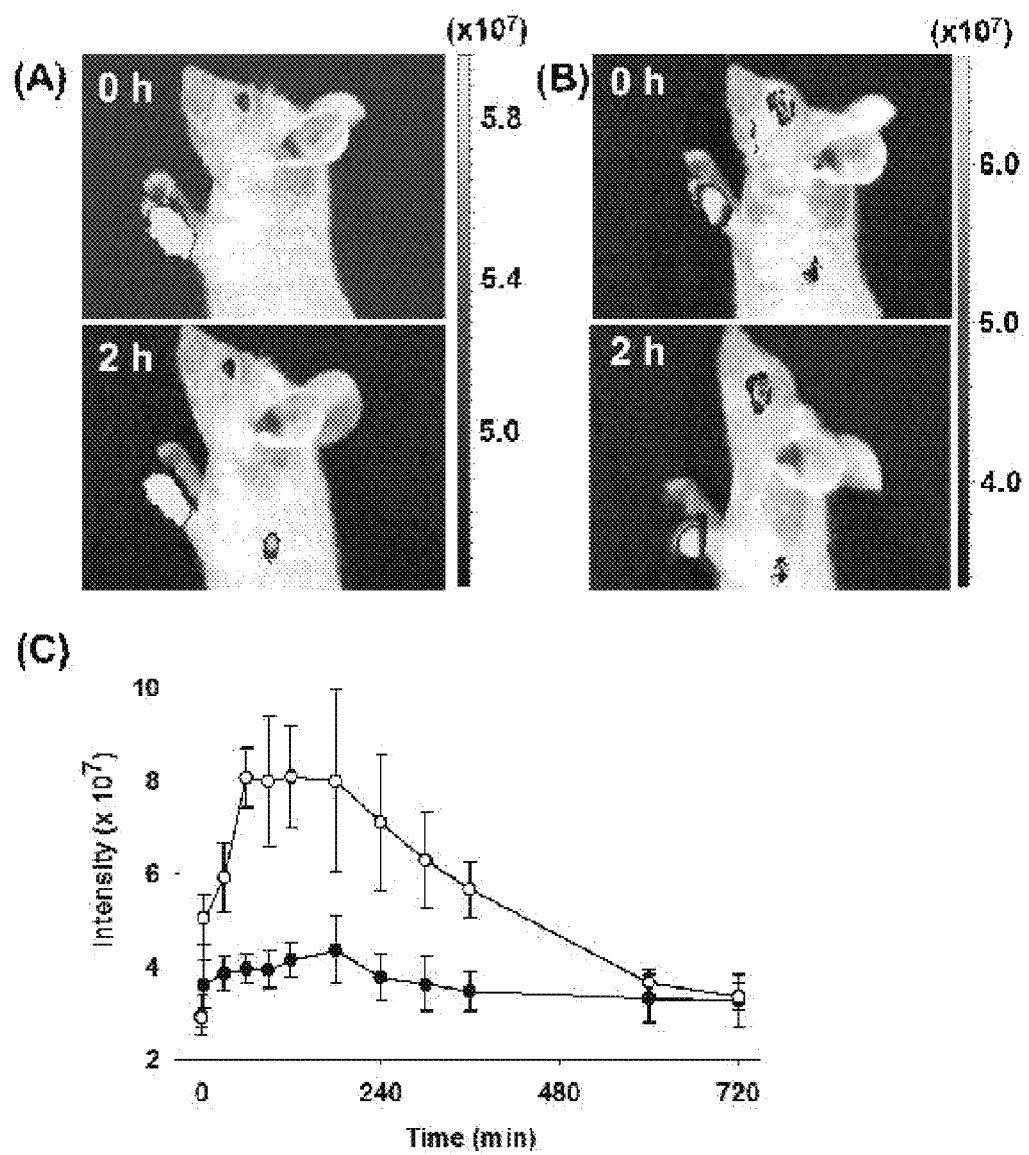

FIG. 2 Gel electrophoresis analysis for stability of Cy5-Ds and Td in 10% mouse serum FIG. 3 SLN imaging by the DNA probes. Mouse images just after (top) and 2 h after (bottom) the injection of Cy5-Td (A) or Cy5-Ds (B). (C) Time-dependent intensity changes of Cy5 emission at the SLN area after injection of Cy5-Td (blank) and Cy5-Ds (filled).

Figure 4:
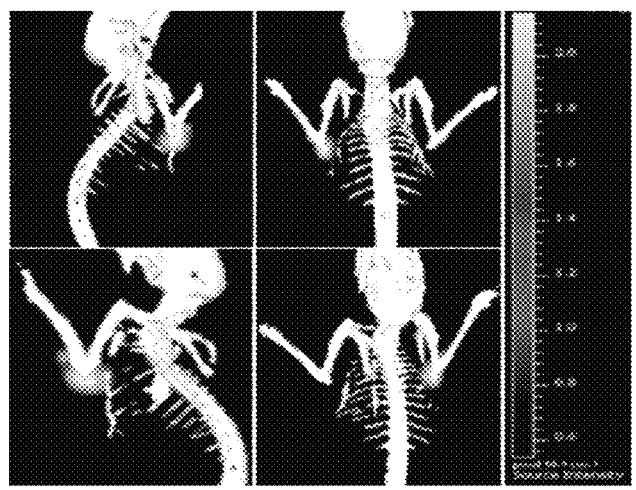

FIG. 4 Optical tomographic images of Cy5-Td injected mouse. SLNs in the left axillary are specifically visualized by the fluorescence emission of Cy5.

Figure 5:
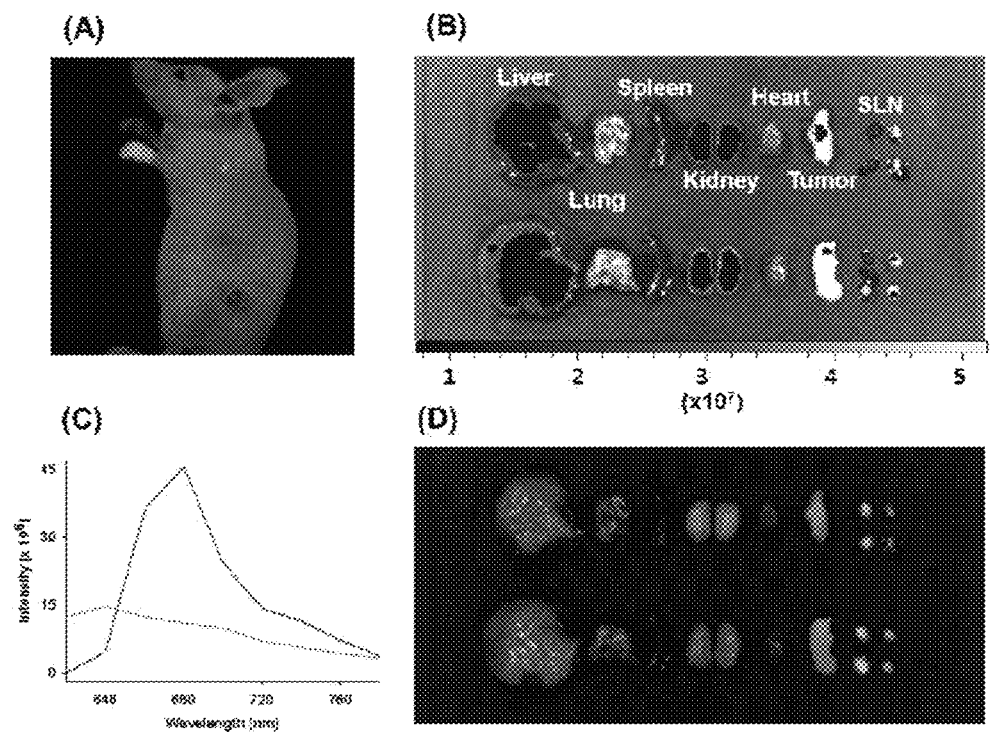

FIG. 5 (A) An in vivo fluorescence image taken at 2 h after administration. (B) Ex vivo NIR fluorescence images of isolated organs from the Cy5-Ds-injected mouse (top) and Cy5-Td-injected mouse (bottom). Organs are displayed one after another from left to right: livers, lungs, spleens, kidneys, hearts, tumors, SLNs in the left axillary, and SLNs in the right axillary. (C) Un-mixed emission profiles of Cy5 (red) and autofluorescence (green) at SNLs. (D) Un-mixed fluorescence images of isolated organs from the Cy5-Ds-injected mouse (top) and Cy5-Td-injected mouse (bottom) indicate Cy5 emission specifically from SLNs in the left axillary.

Figure 6:
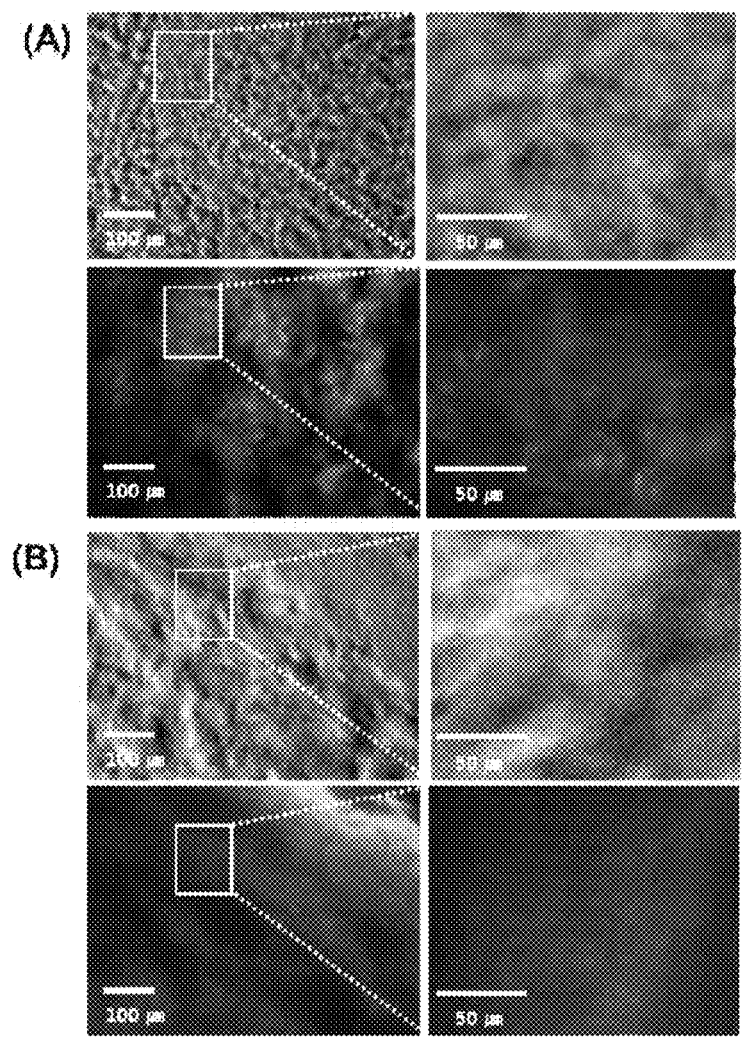

FIG. 6 Fluorescence analysis of the histological localization of Cy-Td (A) and Cy-Ds (B). The zoomed-in images of the squared area in the left panel are shown in the right panel. The bright field images are shown at the top and the corresponding fluorescent images are at the bottom, respectively. Nuclei are stained with DAPI and colored as green.

Figure 7:
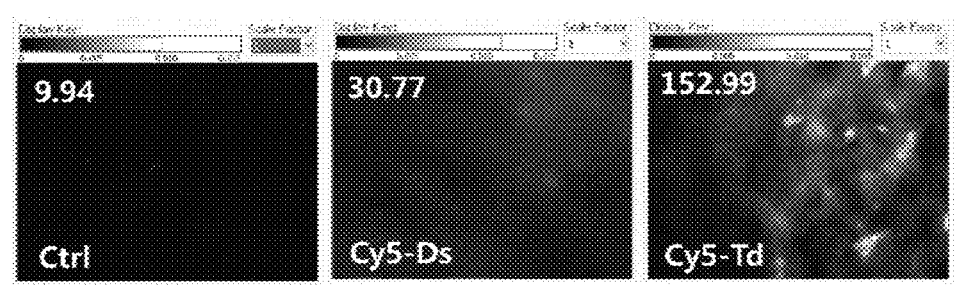

FIG. 7 Intensity comparison in histological images of SLN tissue. The numbers included in the image indicates count level read by the camera and displays average fluorescent signal of Cy5.

Figure 8:
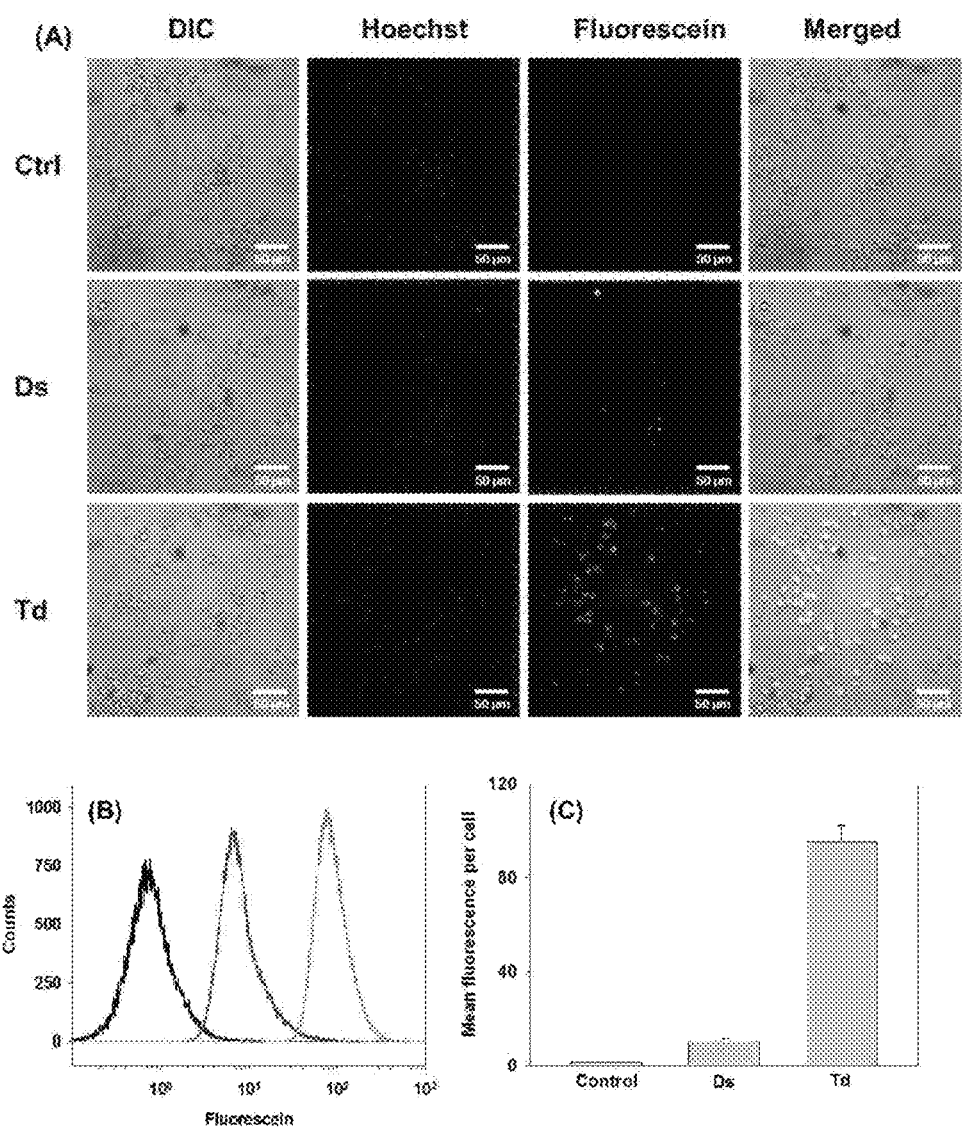

FIG. 8 Cellular uptake of the DNA probes. (A) Fluorescence microscopic images of RAW264.7 cells showing intracellular uptake of Td and Ds. (B) Flow cytometry profiles of the cells treated with Td (green) and Ds (red), compared with that of the untreated control cells (black). (C) Quantitative data showing enhanced cellular uptake of Td compared to Ds.

Figure 9:
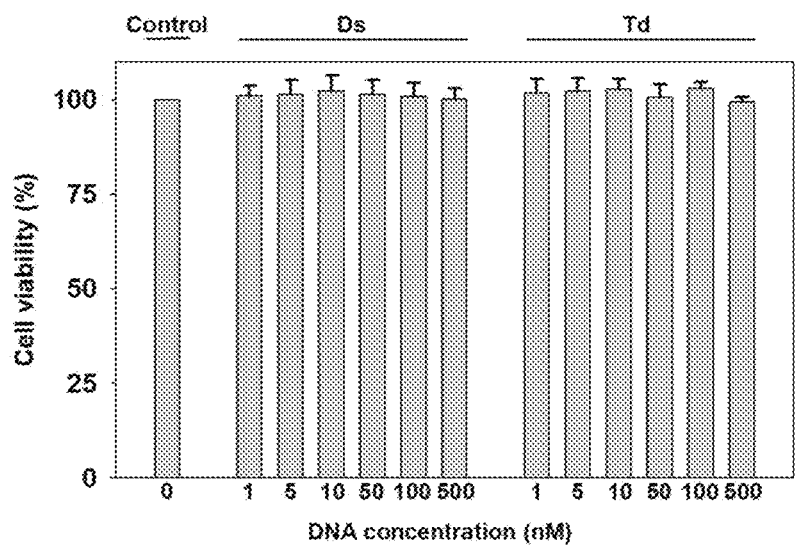

FIG. 9 Cytotoxicity of Ds and Td to RAW264.7.

FIG. 10 Intracellular FRET to examine stability of Td (A) and Ds (B). Images obtained by using excitation and emission filters for the donor (Cy3) are presented at the top rows. Images obtained by using the filters for the acceptor (Cy5) are presented at the bottom rows. FRET images obtained by using the excitation filter for the donor and the emission filter for the acceptor are presented at the middle rows.

FIG. 11 Intracellular FRET. RAW264.7 cells were cultured for 0 (11a), 2 (11b), 4 (11c), 6 (11d), 8 (11e) and 24 hr (11f) after treating with DNA probe.

DETAILED DESCRIPTION OF THE INVENTION

An object to the present invention is to provide a contrast medium composition comprising 3 dimensional DAN nanocage structure and a pharmaceutically acceptable carrier.

The 3 dimensional DNA nanocage structure formed by self-assembly of inherently biocompatible DNA is significantly nuclease resistant compared with common duplex DNA. Noticing that the 3 dimensional DNA nanostructure has flexibility for labelling as well as high bio compatibility and intracellular stability, the inventors designed and performed in vivo bio imagination applying it. As the results, it was identified that the 3 dimensional DNA nanocage structure had improved cellular uptake and intracellular stability astonishingly, so was very suitable for in vivo bio imagination compared with linear DNA duplex.

The DNA nanostructure included in the contrast medium composition of the present invention has a 3 dimensional cage-like structure formed by self-assembly of common linear DNA, for example may have various polyhedron structure such as tetrahedron, hexahedron, octahedron, dodecahedron, icosahedron, and hexakisoctahedron, bipyramids or fullerene like structure, but is not limited thereto. In an preferable example, the 3 dimensional DNA nanocage structure may be tetrahedron.

Especially as the DNA tetrahedron can be prepared by simple assembly of 4 DNA strands with high yield, it is the most practical and particularly the best candidate for SLN contrast medium, because it has a size included in hydrodynamical diameter range (6~10 nm)$^{35}$ required for lymph drainage and lymph node maintenance.

However, the various 3 dimensional DNA nano cage structures other than the DNA tetrahedron also have improved cellular intake and intracellular stability, so can be used as contrast medium nano particles usefully.

In the contrast medium composition in the present invention, the DNA structure may be labelled with inorganic or organic dye, fluorescent substance, isotope, magnetic substance, paramagnetic or super-paramagnetic nanoparticle.

The inorganic or organic dyes which are used for enhancing image contrast in fluorescent or optical image, radiation image like computed tomography (CT), and non-radiation image such as sonogram or MRI including traditional dyes, for example may include diatrizoate, metrizoate, ioxaglate, iopamidol, iohexyl, ioxilan, iopromide, iodixanol, barium based dye like barium sulfate, and Gastrografin®, but are not limited thereto.

The fluorescent substance may include indocyanine, NIR (near infrared) dye, fluorescein, phycoerythrin, rhodamine, lissamine, Cy3, Cy5(Pharmacia), chromophore, chemical luminophore, mass labeling, electron cloud particle, and enzymes (alkaline phosphatase or horseradish peroxidase), but is not limited thereto.

The isotope that can be used for labelling the 3 dimensional DNA nanocage structure of the present invention includes $^{10}C$, $^{11}C$, $^{13}O$, $^{14}O$, $^{15}O$, $^{12}N$, $^{13}N$, $^{15}F$, $^{17}F$, $^{18}F$, $^{32}Cl$, $^{33}Cl$, $^{34}Cl$, $^{43}Sc$, $^{44}Sc$, $^{45}Ti$, $^{51}Mn$, $^{52}Mn$, $^{52}Fe$, $^{53}Fe$, $^{55}Co$, $^{56}Co$, $^{58}Co$, $^{61}Cu$, $^{62}Cu$, $^{62}Zn$, $^{63}Zn$, $^{64}Cu$, $^{65}Zn$, $^{66}Ga$, $^{66}Ge$, $^{67}Ge$, $^{68}Ga$, $^{69}Ge$, $^{69}As$, $^{70}As$, $^{70}Se$, $^{71}Se$, $^{71}As$, $^{72}As$, $^{73}Se$, $^{74}Kr$, $^{74}Br$, $^{75}Br$, $^{76}Br$, $^{77}Br$, $^{77}Kr$, $^{78}Br$, $^{78}Rb$, $^{79}Rb$, $^{79}Kr$, $^{81}Rb$, $^{82}Rb$, $^{84}Rb$, $^{84}Zr$, $^{85}Y$, $^{86}Y$, $^{87}Y$, $^{87}Zr$, $^{88}Y$, $^{89}Zr$, $^{92}TC$, $^{93}TC$, $^{94}TC$, $^{95}TC$, $^{95}RU$, $^{95}Rh$, $^{96}Rh$, $^{97}Rh$, $^{98}Rh$, $^{99}Rh$, $^{100}Rh$, $^{101}Ag$, $^{102}Ag$, $^{102}Rh$, $^{103}Ag$, $^{104}Ag$, $^{105}Ag$, $^{106}Ag$, $^{108}In$, $^{109}In$, $^{110}In$, $^{115}Sb$, $^{116}Sb$, $^{117}Sb$, $^{115}Te$, $^{116}Te$, $^{117}Te$, $^{117}I$, $^{118}I$, $^{118}Xe$, $^{119}Xe$, $^{119}I$, $^{119}Te$, $^{120}I$, $^{120}Xe$, $^{121}Xe$, $^{121}I$, $^{122}I$, $^{123}Xe$, $^{124}I$, $^{126}I$, $^{128}I$, $^{131}I$, $^{129}La$, $^{130}La$, $^{131}La$, $^{132}La$, $^{133}La$, $^{135}La$, $^{136}La$, $^{140}Sm$, $^{141}Sm$, $^{142}Sm$, $^{144}Gd$, $^{145}Gd$, $^{145}Eu$, $^{146}Gd$, $^{146}Eu$, $^{147}Eu$, $^{147}Gd$, $^{148}Eu$, $^{150}Eu$, $^{190}Au$, $^{191}Au$, $^{192}Au$, $^{193}Au$, $^{193}Tl$, $^{194}Tl$, $^{194}Au$, $^{195}Tl$, $^{196}Tl$, $^{197}Tl$, $^{198}Tl$, $^{200}Tl$, $^{200}Bi$, $^{202}Bi$, $^{203}Bi$, $^{205}Bi$, $^{206}Bi$, and their derivatives, but is not limited thereto.

The 3 dimensional DNA nanocage structure of the present invention can be labelled with magnetic substance, paramagnetic or super-paramagnetic nanoparticle, which can be applied particularly in imagination using MRI usefully.

The magnetic substance, paramagnetic or super-paramagnetic nanoparticle, which is a material able to induce spin-lattice relaxation, may include Magnevist (Schering, Germany), Gd chelating compounds such as Gd-DTPA (Gd-diethylene triamine pentaacetic acid), $Gd_2O_3$ (C. Riviere et al. *J. Am. Chem. Soc.* 2007, 129, 5076.), and MnO (T. Hyeon et al. *Angew. Chem. Int. Ed.* 2007, 46, 5397.), but is not limited thereto.

The super-paramagnetic nanoparticle, which is magnetized by externally given magnetic field, affects spin-spin process of hydrogen nuclear-spin in surrounding water molecules by generating a induced magnetic field, and shows dark or negative contrast effect compared with common water by amplifying MRI signal, may include Feridex, Resovist, Combidex, and MEIO (magnetism engineered iron oxide) including oxidized steel substances, but is not limited thereto.

As mentioned in the above, the contrast medium composition can be used appropriately for fluorescence imaging, optical imaging, radiation imaging, computed tomography (CT) or MRI.

The contrast medium composition of the present invention also includes pharmaceutically acceptable carrier with the said 3-dimensional DNA nanocage structures. The pharmaceutically acceptable carrier is usually used in manufacturing medicine and includes lactose, dextrose, sucrose, sorbitol, mannitol, starch, acacia rubber, calcium phosphate, alginate, gelatin, calcium silicate, microcrystal cellulose, polyvinyl pyrrolidone, cellulose, water, syrup, methyl cellulose, methylhydroxy benzoate, hydroxypropylbenzoate, talcum, magnesium stearate and mineral oil, but is not limited thereto. The suitable pharmaceutically acceptable carrier and agent are described in *Remington's Pharmaceutical Sciences* (19th ed., 1995) in detail.

The contrast medium composition of the present invention can be administrated in parenteral or oral manner. In parenteral administration manner, intravenous, intramuscular, intra-articular, intra-synoviral, intra-thecal, intra-hepatic, intra-lesional or intra-cranial injection may be used. Appropriate amount of the contrast medium composition of the present invention may be prescribed variously according to factors including formulation methods, administration manners, patient's age, weight, gender, disease status, food, administration time, route, excretion speed and response susceptibility.

In addition, the contrast medium composition can be used for diagnosing disease by imagination of tissue, and particularly can be used preferably in diagnosis of cancer or canter metastasis.

Another object of the present invention is to a method of bio imagination using the contrast medium composition to provide information for diagnosing development or progression of disease.

As the contrast medium composition of the present invention includes biocompatible 3 dimensional DNA nanocage structure with improved cellular uptake and excellent intracellular stability, it can be used for imagination of biological tissues very usefully.

In a preferable example, the tissue to be visualized may be SLNs (Sentinel Lymph Nodes), which have been difficult to investigate with traditional contrast media because they are surrounded by permeable lymphatic vessel, so have rapid drainage speed. Nevertheless, the contrast medium composition of the present invention is taken and maintained into the cells of the SLNs and shows increased retention time in the SLNs, so has a characteristic to localize even the SLNs which was difficult to investigate due to rapid reflux.

As mentioned above, the method of the present invention which is a method to visualize even SLNs, can be used for diagnosis of cancer or cancer metastasis, and preferably can be performed in vivo.

EFFECTS OF INVENTION

The contrast medium composition of the present invention includes a biomolecule, DNA nanostructure, as an active ingredient, is fundamentally non-cytotoxic and non-immunogenic and is not likely to induce safety problems that may be observed in other organic or inorganic contrast medium composition. In addition, the contrast medium composition of the present invention not only facilitates diagnosis of disease through sufficient contrast enhancement effect by showing excellent cellular uptake and intracellular stability and can visualize even SLNs difficult to be visualized traditionally, so can judge metastasis of cancer easily and apply lower invasive treatment.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

EXAMPLES

<Methods>

Preparation of DNA Tetrahedron (Td) and Linear Double Stranded DNA (Ds).

All DNA oligonucleotides were purchased from Bioneer (Daejeon, Korea). Td was assembled by mixing S1, S2, S3 and Cy5-S4 (or FAM-S4). Four DNA sequences (250 nM of each sequence) were mixed in TM buffer (10 mM Tris-HCl, 5 mM $MgCl_2$, pH=8.0). The mixture was denatured by heating to 95° C. and annealed by cooling to 4° C. using a PCR machine (Applied Biosystems, USA). Ds was made from Cy5-S4 and its complementary strand (c-S4) by adopting the same procedure used for assembling of Td.

The sequences of oligonucleotides used to construct the DNA tetrahedron and the linear duplex DNA were presented in below Table 1.

TABLE 1

(SEQ ID NOS 1, 5, 2-4 and 6-8 respectively, in order of appearance)

| | |
|---|---|
| S1 | 5'-CCAGGCAGTTGAGACGAACATTCCTAAGTCTGAAATTTATCACCCGCCATAGTAGACGTATCA |
| Cy3-S1 | 5'-Cy3-CCAGGCAGTTGAGACGAACATTCCTAAGTCTGAAATTTATCACCCG CCATAGTAGACGTATCA |
| S2 | 5'-CTTGCTACACGATTCAGACTTAGGAATGTTCGACATGCGAGGGTCCAATACCGACGATTACAG |
| S3 | 5'-GGTGATAAAACGTGTAGCAAGCTGTAATCGACGGGAAGAGCATGCCCATCCACTACTATGGCG |
| S4 | 5'-CCTCGCATGACTCAACTGCCTGGTGATACGAGGATGGGCATGCTCTTCCCGACGGTATTGGAC |
| Cy5-S4 | 5'-Cy5-CCTCGCATGACTCAACTGCCTGGTGATACGAGGATGGGCATGCTCTTCCCGACGGTATTGGAC |

TABLE 1-continued

| | |
|---|---|
| FAM-S4 | 5'-fluorescein-CCTCGCATGACTCAACTGCCTGGTGATACGAGGATGGGCATGCTCTTCCCGACGGTATTGGAC |
| c-S4 | 5'-GTCCAATACCGTCGGGAAGAGCATGCCCATCCTCGTATCACCAGGCAGGTGAGTCATGCGAGG |

Gel electrophoresis. Non-denaturing polyacrylamide gels (6%) were run in TBE buffer with 100 V at 4° C. for 40 min to identify formation of DNA tetrahedron (Td). After electrophoresis, the images were visualized using a fluorescence scanner (Typhoon 9400, GE healthcare, USA)

Dynamic light scattering. The hydrodynamic size of Td was measured in Zetasizer (Malvern, UK) by following a literature procedure.[38]

Measurement of nuclease resistance. For stability test, add 10% mouse serum (10 μL, Sigma Aldrich, USA) to DNA solution (90 μL, 900 nM) and incubate the mixture at 37° C. At each time point, stop the reaction by adding stop solution comprising 98% deionized formamide, 10 mM EDTA, bromophenol blue and xylenecyanol 0.5 mg/ml and perform analysis on denaturated 12% PAGE (7 M urea). Amount of undamaged DNA structure was measured by visualizing Cy5-S4 on the fluorescent scanner (Typhoon9400, GE Healthcare, USA).

SLN mapping by in vivo imaging. The animal study was approved by the animal care and use committee of Korea Institute of Science and Technology and all mice were handled in accordance with institutional regulations. For in vivo imaging and disease model preparation, mice were anaesthetized with intraperitoneal injection of 0.5% pentobarbital sodium (0.01 mL/g). Animal disease models were prepared on BALB/c nude mice (male, 5 weeks old, Orient Bio Inc., Korea). Tumors were established by subcutaneous inoculation of SCC7 cells ($1.0 \times 10^6$ cells suspended in the culture medium) into the thigh of mice. Cy5-Ds and Cy5-Td were intradermally injected into the left forepaw pad. The real-time fluorescence of SLN mapping was recorded using a CCD camera, implemented in a high-sensitivity imaging system (IVIS-spectrum, Perkin-Elmer, USA).

Ex vivo imaging and histologic analysis. After in vivo imaging studies, ex vivo near-infrared fluorescence images of resected organs, lymph nodes and the rest of the body were taken by a IVIS-spectrum imaging system with the same acquisition setup as used for the in vivo imaging. For optical and fluorescent histologic inspection, DAPI (4',6'-diamidino-2-phenylindole)-stained sections (20 μm, CM1900 microtome, Leica, Germany) of the OCT-embedded lymph nodes were investigated on microscopes (Leica DM13000 B, Germany and Nuance Multispectral Imaging System, Perkin Elmer, USA).

Transfection of Td into RAW264.7 cells. RAW264.7 cells were plated in glass-bottomed 35 mm petri dishes with DMEM media (Gibco, USA) containing 10% heat inactivated fetal bovine serum, 1% penicillin and streptomycin. After $2.5 \times 10^4$ cells were seeded in each dish, the dishes were incubated overnight at 37° C. in humidified atmosphere containing 5% $CO_2$. The growth medium was removed from each cell sample, and the cells were washed twice with PBS (Gibco, USA). Each transfection mixture was made using Td or Ds (250 nM) in the fresh medium (250 μL) without serum and the antibiotics, then added to a sample of cells, and incubated for 6 h at 37° C. in humidified atmosphere containing 5% $CO_2$.

Microscopic imaging of Td in RAW264.7 cells. For microscopic examination and flow cytometry analysis, FAM-S4 strand was used for the preparation of fluorescently labeled Td. The nuclei were stained using Hoechst 34580 (3 μg/mL, Invitrogen, USA), and the cells were washed with PBS (200 μL) twice. The cell culture medium (200 μL) was then added. Live cells were imaged using a fluorescence microscopy (DeltaVision, Applied Precision, USA). Excitation/emission filters used for fluorescein and Hoechst 34580 were 480-500/509-547 nm, and 340-380/432-482 nm, respectively.

Flow cytometry analysis. RAW264.7 cells were seeded on 24-well culture plates at a density of $10^5$ cells/mL and cultured for 24 h and then washed twice with PBS. They were incubated with the fluorescently labeled DNA molecules by using the same manner adopted for the transfection experiment, harvested, and washed three times with PBS. Then, 0.2 mL of trypsin replacement (TrypLE™, Gibco, USA) was added to each sample, and the samples were incubated for 5 min at 37° C. Then 1 mL of the medium was added to each sample, and the resulting cell suspensions were transferred to conical tubes (Falcon™ tubes, BD Biosciences, USA) and centrifuged for 3 min at 2500 rpm. Supernatant was removed, and the cell pellets were resuspended in 1 mL of PBS. Fluorescence intensity of the cells was estimated by flow cytometry (FC500, Beckman coulter, USA). Samples of at least 1,000 cells were analyzed in triplicate.

Cytotoxicity analysis. Cytotoxicity of Td was measured with MTT analysis. Concretely, $8.0 \times 10^3$ of RAW264.7 cells were seeded into 96-well plate with cell culture medium (100 μL) and culture overnight to ~80% of confluency. Then, the cells were cultured under existence of DS or Td with fresh culture medium without serum and antibiotics in $CO_2$ chamber at 37° C. for 6 hr. The sample containing the medium was removed and the cells were washed with PBS 3 times. The cells were cultured with fresh culture medium in $CO_2$ chamber for 48 hr. Then, Add 10 μL of thiazolyl blue tetrazolium bromide (MTT, TAGS, Germany) was added to each cell and culture the cells at at 37° C. for 4 hr. The cells were eluted with 200 μL of dimethyl sulfoxide (DMSO, Sigma-Aldrich, USA). After culturing at RT overnight, optical density was measured at 580 nm using a microplate reader (SpectraMax Plus™, Molecular Devices, USA).

Fluorescence resonance energy transfer (FRET) analysis. RAW264.7 cells were plated in glass-bottomed 35 mm petri dishes with DMEM media (Gibco, USA) containing 10% heat inactivated fetal bovine serum, 1% penicillin and streptomycin. After $2.5 \times 10^4$ cells were seeded in each dish, the dishes were incubated overnight at 37° C. in humidified atmosphere containing 5% $CO_2$. The growth medium was removed from each cell sample, and the cells were washed twice with PBS (Gibco, USA). Cy3-Td-Cy5 was assembled by mixing Cy3-S1, S2, S3, and Cy5-S4. Cy3-Ds-Cy5 was prepared by mixing Cy3-c-S4 and Cy5-S4. Mono-labeled control probes for Td and Ds were prepared by mixing Cy3-S1, S2, S3, and S4 (or 51, S2, S3, and Cy5-S4) and S4 and Cy3-S1 (or 51 and Cy5-S4), respectively. The mixtures were denatured by heating to 95° C. and annealed by cooling to 4° C. using a PCR machine. The transfection was performed by using the same manner adopted for the uptake experiment. Final concentration of DNA samples were 100 nM. Then, the cells were washed twice by PBS, and incubated with fresh cell culture medium (200 μL) at 37° C., and imaged at different time points (0, 2, 4, 6, 8, and 24 h) using a fluorescence microscopy (Delta Vision). Excitation/emission filters used for Cy3 and Cy5 were 542-570/594-630 and 630-650/665-705 nm, respectively. For FRET analysis, the signals were recorded using different excitation/emission filters such as Cy3/Cy3 (donor/donor), Cy3/Cy5 (donor/acceptor) and Cy5/Cy5 (acceptor/acceptor) and analyzed by ImageJ <Results>

Figure 1:
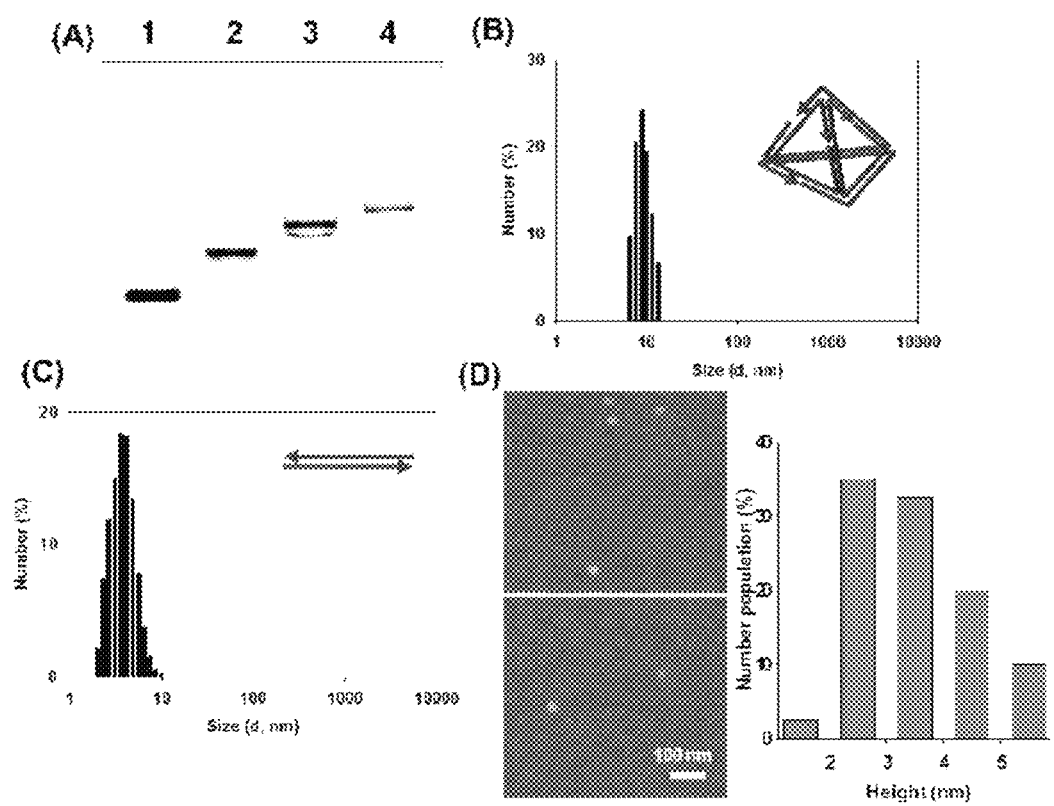
FIG. 1 Characterization of Td. (A) Native PAGE to verify assembly of the tetrahedron. Lane 1: Cy5-S4; Lane 2: Cy5-S4 and S3; Lane 3: Cy5-S4, S3, and S2; Lane 4.

Construction of the DNA tetrahedron structure (Td) was analyzed on a non-denaturing polyacrylamide gel electrophoresis (PAGE). The incremental retardation by strand-wise addition of DNA, the typical phenomenon in assembly of DNA tetrahedron, was observed in the PAGE analysis (FIG. 1A). For the size determination, dynamic light scattering (DLS) was measured for the DNA tetrahedron and compared with the linear duplex DNA (Ds). The sizes of the DNA tetrahedron and the DNA duplex were 8.89 (±0.22) nm and 4.19 (±0.39) nm, respectively (FIGS. 1B and 1C). AFM was additionally measured for further characterization, and the sizes of DNA tetrahedron observed in the AFM images were 3-5 nm at the dried state (FIG. 1D).

To estimate the serum stability of the DNA nanostructures, the nuclease resistance of the Cy5-labeled Td (Cy5-Td) was examined in 10% mouse serum solution. More than 70% of the tetrahedron structure survived after 7 h exposure to the serum solution, whereas complete degradation of linear duplex DNA (Cy5-Ds) was observed after 3 h (FIG. 2). This hour-long serum stability of Td would be an advantageous property for SLN imaging, since the SNL biopsy operation takes about 30 min after visualization of SLNs.[36]

After characterization of the DNA tetrahedron assembly and analysis of its stability in serum, visualization of SLNs was attempted by subcutaneous injection of the Cy5-labeled DNA construct (Cy5-Td) in the forepaw of tumor-bearing mice. As SLNs of forepaws are usually located in axillary regions, the fluorescence signal through the skin of the axillary region was monitored to assign SLNs. FIG. 3 presents the fluorescence images of mice after injection of the DNA probes. SLNs in an axillary could be detected successfully by using Cy5-Td as the imaging probe (FIG. 3A), whereas the linear DNA probe, Cy5-Ds showed negligible fluorescence signal in SLNs and failed to provide spatial information of SLNs (FIG. 3B). In contrast to the specific localization of Cy5-Td in SLNs, Cy5-Ds was observed in an undesired region such as face. To obtain kinetic information about SLN imaging by the probes, fluorescence intensity of each probe at the lymph node was quantified (FIG. 3C). The fluorescence intensity level reached to the maximum level at 2 h after the injection of Cy5-Td. The intensity decreased slowly to the background level for the next 8 h. In contrast to the tetrahedron structure, the linear DNA provided the intensity level that was hardly distinguishable from the background signal during the measurement. These results suggest that the DNA tetrahedron could be used for SLN imaging and that the nanoparticle-like structure is inevitable for DNA materials to be utilized in the application. The translocation of the Cy5-Td in SLNs of the axillary was additionally demonstrated by the tomographic images of the probe-injected mouse as shown in FIG. 4.

After observing specific SLN imaging by Cy5-Td in live animals (FIG. 5A), biodistribution of the fluorescent DNA tetrahedron was monitored in the mouse sacrificed 2 h after injection. Fluorescence from Cy5 labeled on the DNA tetrahedron indicated that the Cy5-Td probe was accumulated mainly in SLNs, with small amount in the kidney, liver, and spleen (top in FIG. 5B) On the contrary, the linear DNA probe, Cy5-Ds exhibited relatively low uptake in SLNs and accumulated similarly to other organs containing the probe (bottom in FIG. 5B). The difference in the emission spectra between other tissues and SLNs indicated that the distinct fluorescence intensity observed in the SLNs was due to Cy5 labeled on the DNA tetrahedron, which excluded the possibility of non-specific imaging resulting from autofluorescence of the tissues (FIG. 5C and 5D).

After observing efficient imaging of SLNs by Cy5-Td, the distribution of the DNA constructs in the SLN tissues was investigated by histological analysis of the nodes. The fluorescence intensity of Cy5 in the frozen sections indicated that the majority of Cy5-Td was taken up by cells in the sinusoidal region, which could be identified by the fluorescence emission (FIG. 6A). In contrast, Cy5-Ds was scarcely accumulated in the cells, showing a diffuse and dim staining pattern (FIG. 6B). The relative intensity of the Cy5-Td-treated tissues was about five times higher than that of Cy5-Ds-treated ones which was as low as the control background signal (FIG. 7).

To further examine the cellular internalization of the DNA constructs observed during in vivo SLN imaging, in vitro studies on cellular uptake of the DNA constructs were also carried out in RAW264.7 mouse macrophage precursor cells. RAW264.7 was chosen as a model system for in vitro cellular studies since macrophages are one of various cell types found in lymph nodes.[37] When the fluorescein-labeled DNA tetrahedron was incubated with RAW264.7 cells for 6 h, cytoplasm of the cells became fluorescent under the microscopy suggesting that Td was successfully delivered into the cells (FIG. 8A). The delivery of Ds, however, was not as effective as Td. For quantitative analysis of the uptake of the DNA constructs in cells, the delivery efficiency was analyzed by flow cytometry (FIGS. 8B and 8C). Relatively enhanced delivery of Td was observed compared with Ds, which was consistent with the microscopic images.

In terms of cytotoxicity of the DNA tetrahedron, Td did not influence on the cell viability, indicating that the DNA nanoconstruct is non-cytotoxic (FIG. 9).

Figure 10A:
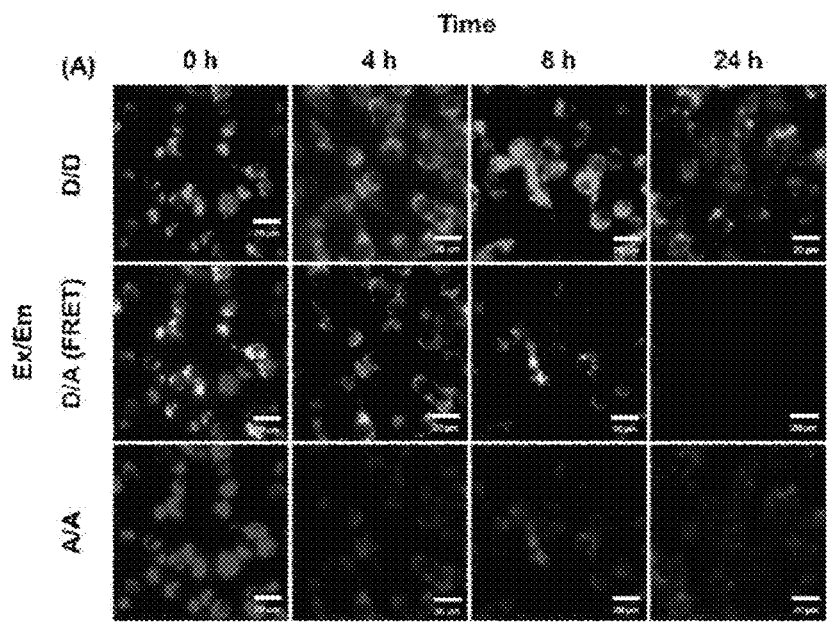
Figure 10B:
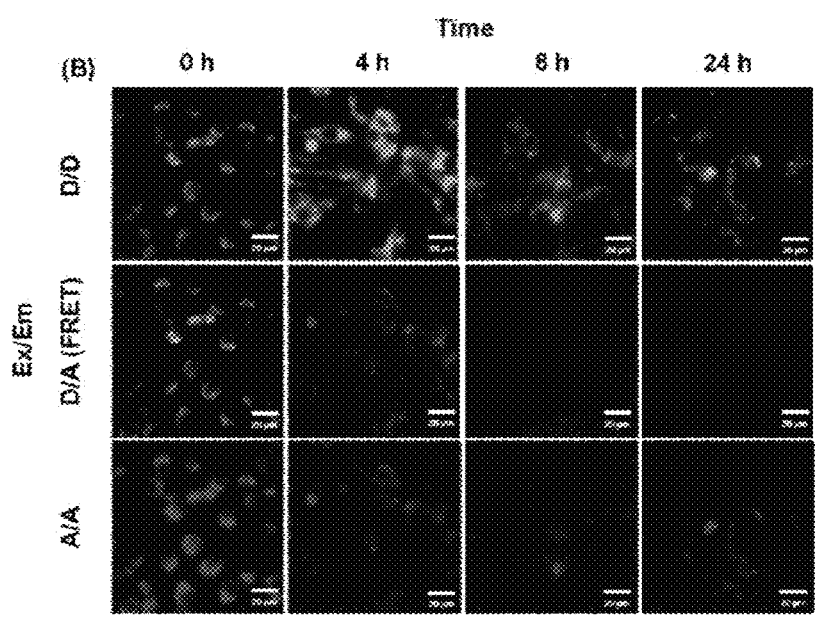
Figure 11A:
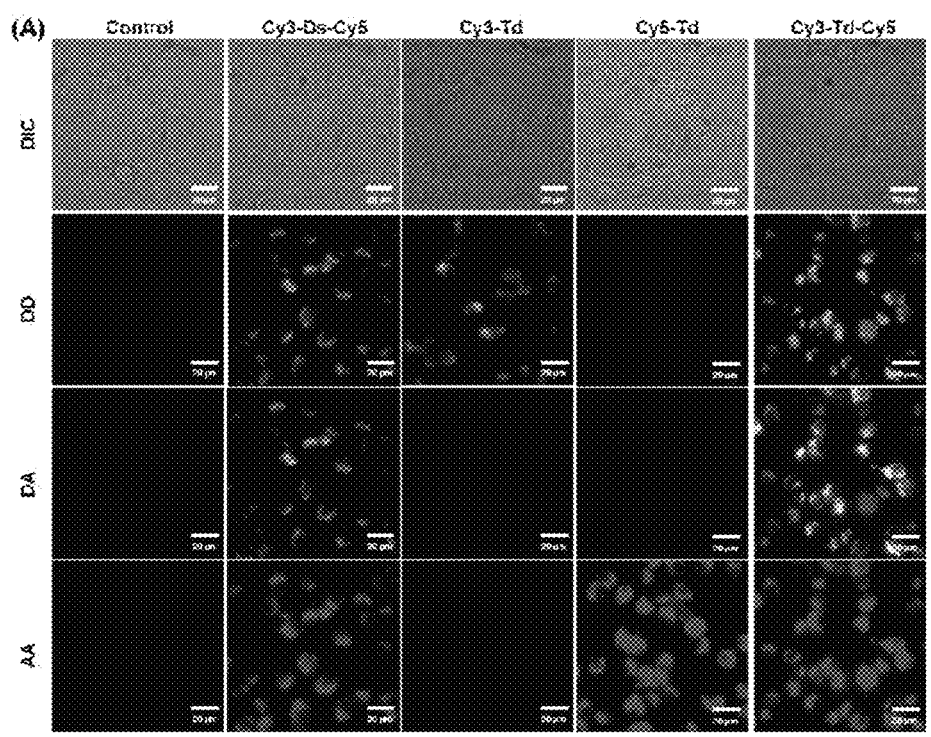
Figure 11B:
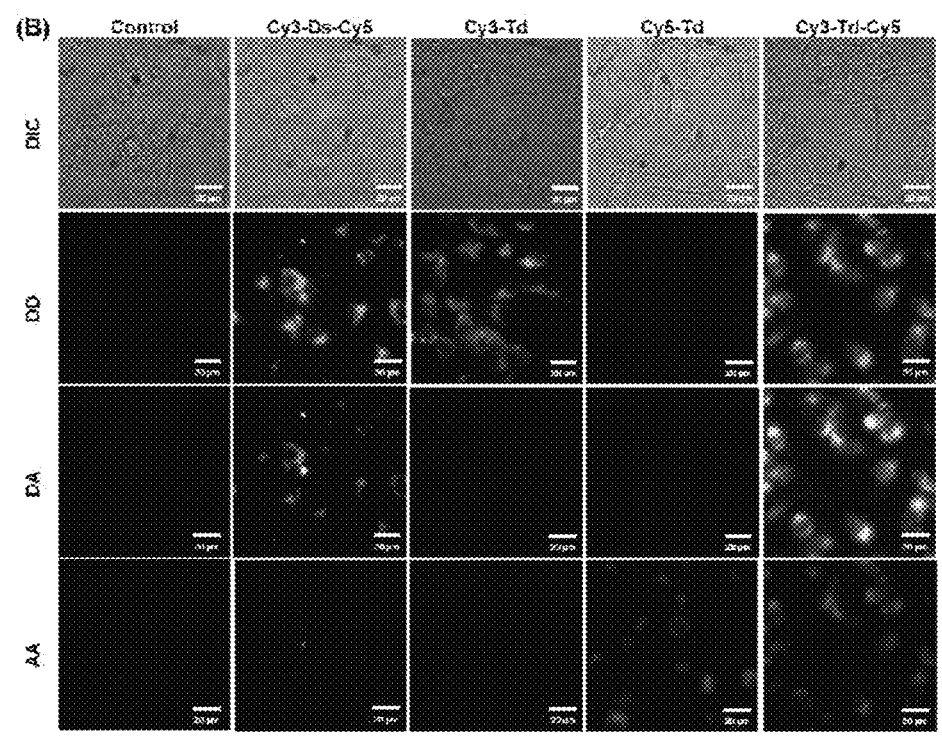
Figure 11C:
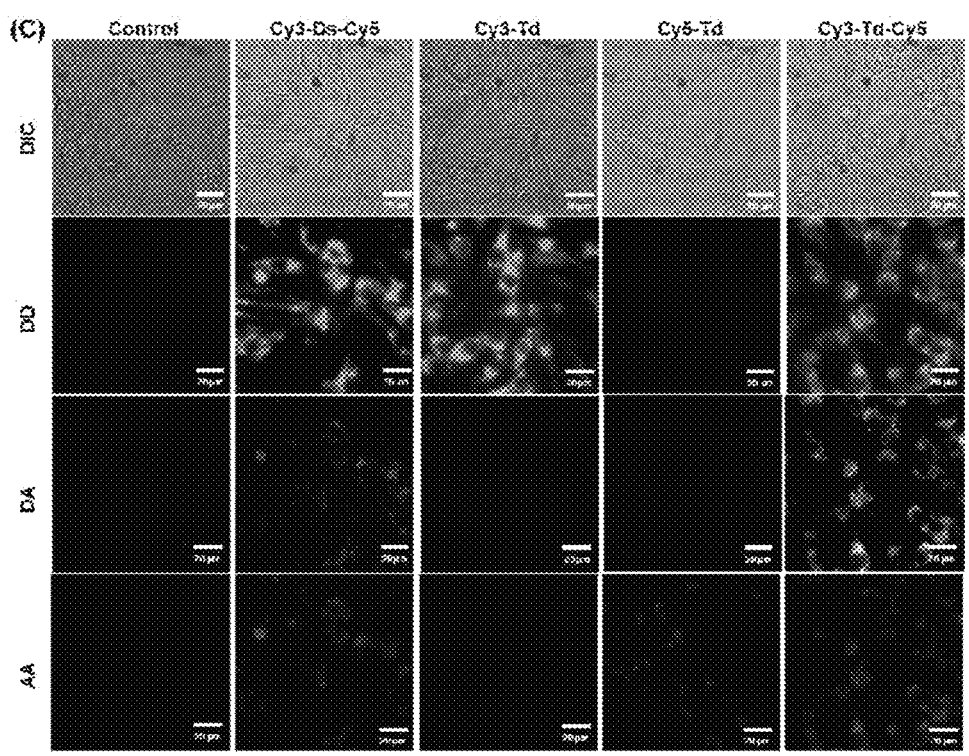
Figure 11D:
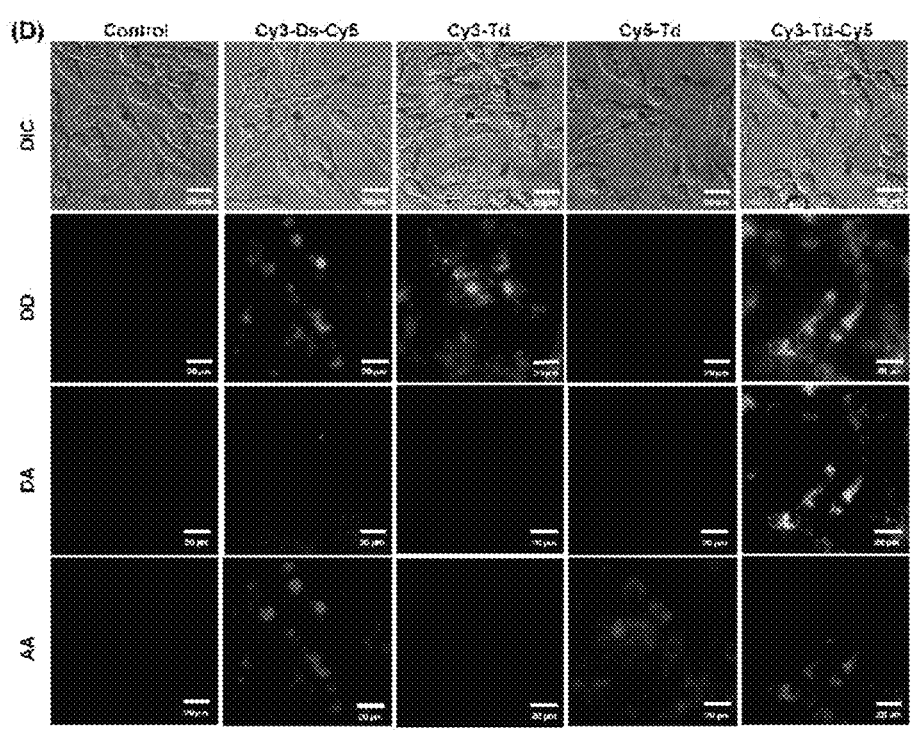
Figure 11E:
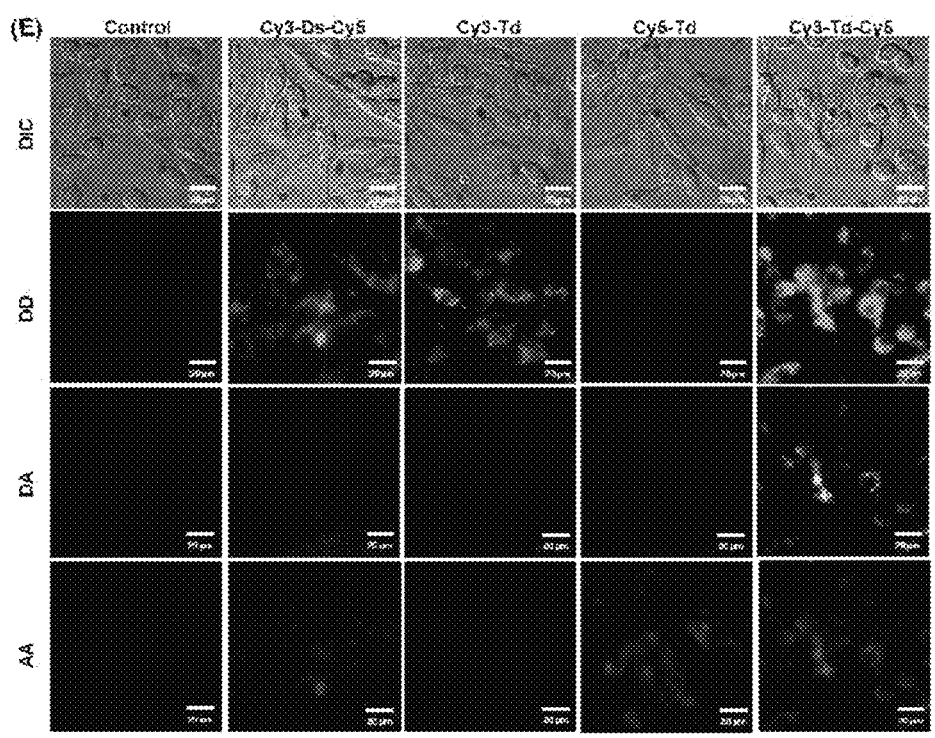
Figure 11F:
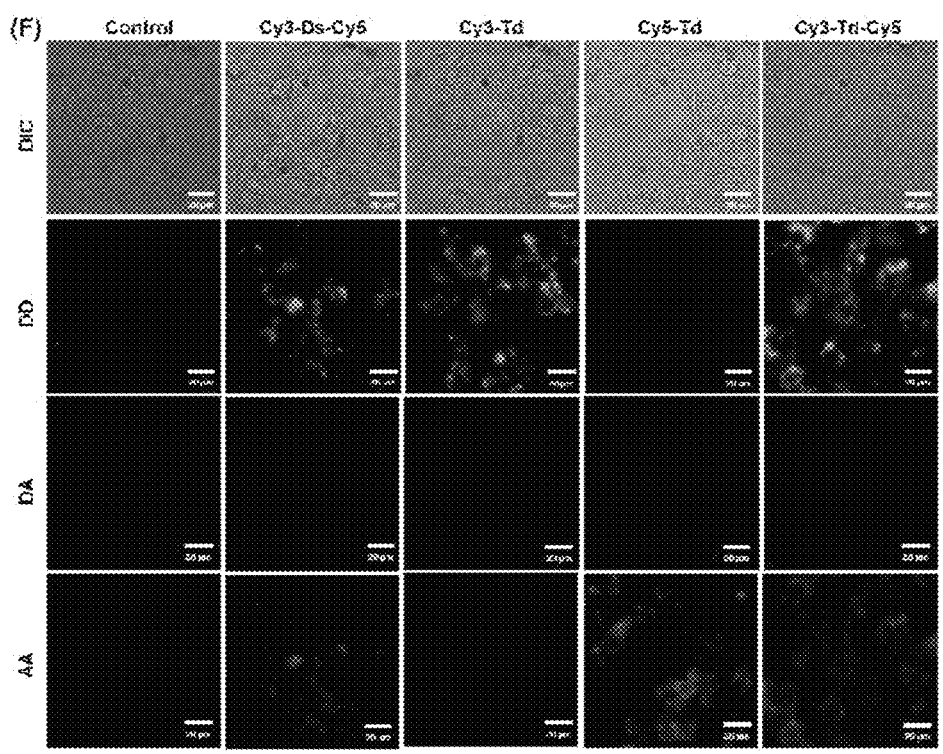

Intracellular stability of the tetrahedron assembly was also investigated by monitoring fluorescence resonance energy transfer (FRET) efficiency of the dually labeled Cy3-Td-Cy5. Emission profiles were obtained after irradiation of the excitation light for the donor on the cells treated with Cy3-Td-Cy5. The FRET signal was monitored as the ratio of increased acceptor intensity at 670 nm to the decreased donor intensity at 580 nm (FIG. 10 and FIG. 11). The intensity of cells treated with the mono-labeled Cy3-Td and Cy5-Td were used as the background controls. Increased concentration of DNA probes (100 nM) were used for fluorescent cellular images. FIG. 10a shows intracellular FRET images of Td at different time points. Although time-dependent decreases were observed not only in Cy3 and Cy5 intensities but also in FRET efficiency, FRET-based signals were still observed even after 8 h in the cells treated with Td, showing a considerable intracellular stability of Td consistent with the previous result.[31-32] In contrast, the FRET signal from the linear Cy3-Ds-Cy5 decreased rapidly and reached nearly to the background level after 4 h (FIG. 10b), well correlated with the tendency of the in vitro serum stability evaluation (FIG. 11). These results suggest that the successful SLN imaging by the DNA tetrahedron is due to increased cellular uptake and improved intracellular stability of the tetrahedron structure compared to the linear duplex in macrophage cells of SLNs.

<Conclusion>

In the above examples, the inventors utilized a nano-sized DNA tetrahedron for efficient SLN imaging based on fluorescence of the Cy5 label on the DNA construct. The visualization of SLNs by the dye-labeled DNA nanoconstruct was successfully demonstrated in an in vivo model system. Compared with the linear DNA probe, the DNA tetrahedron showed enhanced translocation in SLNs and prolonged retention time at the node. These advantageous properties of DNA tetrahedron for SLN mapping were due to enhanced cellular uptake of the DNA construct.

The efficiency of cellular uptake and the improved intracellular stability of the DNA tetrahedron were evaluated by in vitro FRET assays using mouse macrophage precursor cells. The tetrahedron is remarkably resistant to nuclease, which makes the DNA tetrahedron a more attractive tool in in-vivo imaging technique.

Other various three-dimensional nanocage structures as well as the tetrahedron indicate improved cellular uptake and intracellular stability compared with liner duplex DNA, so it is expected that they can be used effectively in SLN mapping.

DNA tetrahedron is composed of inherently biological molecules that can be degraded into metabolic nucleotides, it is virtually non-cytotoxic, non-immunogenic, and has a low potential to cause safety problems that may be observed in other organic or inorganic nanoparticle-based SLN imaging systems when applied in the clinical area. Moreover, not only the fluorescence label but also chemical moieties for other imaging modalities can be easily and site-specifically incorporated into a DNA strand of the tetrahedron. Therefore, with the successful performance in SLN imaging, the high biocompatibility and the simple preparation with an immense potential for tailor-made modification, the DNA tetrahedron is expected to be a useful SLN imaging agent also in the human clinical model.

What is claimed is:

1. A method of bio-imaging a sentinel lymph node, comprising:
   (a) administering parenterally to a subject a contrast medium composition comprising a DNA nanocage, a label, and a pharmaceutically acceptable excipient, wherein the DNA nanocage has a tetrahedral structure, and wherein the tetrahedral structure has 6 sides each consisting of duplex oligonucleotide; and
   (b) detecting a real-time signal derived from the label in the sentinel lymph node of the subject, wherein the detection of the real-time signal indicates development or progression of cancer or cancer metastasis.

2. The method according to claim 1, wherein the label is selected from the group consisting of diatrizoate, metrizoate, ioxaglate, iopamidol, iohexol, ioxilan, iopromide, iodixanol, barium based dye, GASTROGRAFIN®, a fluorescent substance, and an isotope.

3. The method according to claim 1, wherein the real-time signal is visualized using any one selected from a fluorescence imaging, an optical imaging, a radiation imaging, a computed tomography (CT) or a MRI bio-imaging method.

4. The method according to claim 1, wherein the method is carried out in vivo.

5. The method according to claim 1, wherein the step of detecting the real-time signal occurs from 2 to 10 hours after the step of administering.

6. The method according to claim 1, wherein the DNA nanocage has a hydrodynamic diameter range of 6-10 nm.

7. The method according to claim 1, wherein the contrast medium composition has a stability in serum greater than 70% for 3 to 7 hours.

8. The method according to claim 1, wherein the contrast medium composition consists essentially of the DNA nanocage, the label, and the pharmaceutically acceptable excipient.

9. The method according to claim 1, wherein the oligonucleotide is a nucleotide sequence selected from the group consisting of SEQ ID NOs: 1 to 8.

10. The method according to claim 2, wherein the barium based dye is barium sulfate.

11. The method according to claim 2, wherein the fluorescent substance is selected from the group consisting of indocyanine, NIR (near infrared) dye, fluorescein, phycoeryhrin, rhodamine, lissamine, Cy3, Cy5, chromophore, chemical luminophore, horseradish peroxidase, and alkaline phosphatase.

* * * * *

SEQUENCE LISTING

```
<160> NUMBER OF SEQ ID NOS: 8

<210> SEQ ID NO 1
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccaggcagtt gagacgaaca ttcctaagtc tgaaatttat cacccgccat agtagacgta     60
tca                                                                  63

<210> SEQ ID NO 2
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cttgctacac gattcagact taggaatgtt cgacatgcga gggtccaata ccgacgatta     60
cag                                                                  63

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggtgataaaa cgtgtagcaa gctgtaatcg acgggaagag catgcccatc cactactatg     60
gcg                                                                  63

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
```

-continued

```
cctcgcatga ctcaactgcc tggtgatacg aggatgggca tgctcttccc gacggtattg    60
gac                                                                  63
```

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Cy3

<400> SEQUENCE: 5

```
ccaggcagtt gagacgaaca ttcctaagtc tgaaatttat cacccgccat agtagacgta    60
tca                                                                  63
```

<210> SEQ ID NO 6
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Cy5

<400> SEQUENCE: 6

```
cctcgcatga ctcaactgcc tggtgatacg aggatgggca tgctcttccc gacggtattg    60
gac                                                                  63
```

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-fluorescein

<400> SEQUENCE: 7

```
cctcgcatga ctcaactgcc tggtgatacg aggatgggca tgctcttccc gacggtattg    60
gac                                                                  63
```

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
gtccaatacc gtcgggaaga gcatgcccat cctcgtatca ccaggcagtt gagtcatgcg    60
agg                                                                  63
```